US011458006B2

(12) United States Patent
Dinges et al.

(10) Patent No.: US 11,458,006 B2
(45) Date of Patent: Oct. 4, 2022

(54) AORTIC GRAFT OCCLUDER

(71) Applicant: PMU Innovations GMBH, Salzburg (AT)

(72) Inventors: Christian Dinges, Salzburg (AT); Johann Fierlbeck, Salzburg (AT)

(73) Assignee: PMU INNOVATIONS GMBH, Salzburg (AT)

(*) Notice: Subject to any disclaimer, the term of this patent is extended or adjusted under 35 U.S.C. 154(b) by 346 days.

(21) Appl. No.: 16/610,605

(22) PCT Filed: May 7, 2018

(86) PCT No.: PCT/EP2018/061703
§ 371 (c)(1),
(2) Date: Nov. 4, 2019

(87) PCT Pub. No.: WO2018/206495
PCT Pub. Date: Nov. 15, 2018

(65) Prior Publication Data
US 2020/0060806 A1    Feb. 27, 2020

(30) Foreign Application Priority Data
May 8, 2017    (EP) .................................... 17169992

(51) Int. Cl.
*A61F 2/06*    (2013.01)
*A61B 17/12*    (2006.01)
(52) U.S. Cl.
CPC ............ *A61F 2/06* (2013.01); *A61B 17/1204* (2013.01); *A61F 2240/008* (2013.01)
(58) Field of Classification Search
CPC .... A61F 2240/008; A61F 2/06; A61F 2/2472;
A61F 2/00; A61F 2/24; A61F 2/07; A61F 2002/077; A61F 2/2427; A61B 17/11;
G01M 3/2876; G01M 3/00; G01M 3/02;
G01M 3/26
(Continued)

(56) References Cited

U.S. PATENT DOCUMENTS

| 1,846,311 | A | * | 2/1932 | Clare | ................... | G01M 3/2876 |
| | | | | | | 116/34 R |
| 5,333,490 | A | * | 8/1994 | Webb | ................... | B67D 7/3209 |
| | | | | | | 73/40.5 R |
| 8,430,836 | B2 | * | 4/2013 | Vassiliades | ......... | A61M 27/002 |
| | | | | | | 604/8 |

(Continued)

FOREIGN PATENT DOCUMENTS

CN    1218378 A    6/1999
CN    1304297 A    7/2001
(Continued)

OTHER PUBLICATIONS

International Search Report and Written Opinion for International application No. PCT/EP2018/061703, dated Jun. 20, 2018, 10 pages.

*Primary Examiner* — Tuan V Nguyen
*Assistant Examiner* — Bridget E. Rabaglia
(74) *Attorney, Agent, or Firm* — Seager, Tufte & Wickhem, LLP

(57) ABSTRACT

An aortic graft occluder for intraoperative leak testing of a tubular aortic graft attached to an aortic root. The aortic graft occluder includes a plug adapted for sealingly closing an opening of the aortic graft. The plug includes a first pathway adapted for connecting a lumen of the aortic graft with a feed line.

16 Claims, 12 Drawing Sheets

(58) Field of Classification Search
USPC ...... 623/1.25, 1.23, 2.11, 913, 912; 606/153
See application file for complete search history.

(56) References Cited

U.S. PATENT DOCUMENTS

| | | | |
|---|---|---|---|
| 2003/0204270 A1 | 10/2003 | Berman et al. | |
| 2004/0092892 A1 | 5/2004 | Kagan et al. | |
| 2005/0020998 A1* | 1/2005 | Bonnette | A61M 25/1018 |
| | | | 604/509 |
| 2005/0203549 A1* | 9/2005 | Realyvasquez | A61B 17/11 |
| | | | 623/2.11 |
| 2009/0112053 A1 | 4/2009 | Viitala et al. | |
| 2013/0090715 A1 | 4/2013 | Chobotov | |
| 2014/0276326 A1* | 9/2014 | Gollner | A61M 39/1011 |
| | | | 604/6.16 |
| 2017/0086964 A1 | 3/2017 | Sperling | |

FOREIGN PATENT DOCUMENTS

| | | |
|---|---|---|
| CN | 1403170 A | 3/2003 |
| CN | 1984621 A | 6/2007 |
| CN | 201076529 Y | 6/2008 |
| CN | 101384228 A | 3/2009 |
| CN | 201359550 Y | 12/2009 |
| CN | 102551919 A | 7/2012 |
| CN | 202290067 U | 7/2012 |
| CN | 102641164 A | 8/2012 |
| CN | 102917668 A | 2/2013 |
| CN | 102970944 A | 3/2013 |
| CN | 103841929 A | 6/2014 |
| CN | 104334121 A | 2/2015 |
| CN | 105142574 A | 12/2015 |
| CN | 105142578 A | 12/2015 |
| CN | 105486457 A | 4/2016 |
| CN | 105877873 A | 8/2016 |
| CN | 105899141 A | 8/2016 |
| CN | 205826236 U | 12/2016 |
| CN | 106456217 A | 2/2017 |
| GN | 101305942 A | 11/2008 |
| WO | 03009780 A2 | 2/2003 |
| WO | 2012141679 A1 | 10/2012 |
| WO | 2018206495 A1 | 11/2018 |

* cited by examiner

AORTIC GRAFT OCCLUDER

This is a national stage application filed under 35 U.S.C. § 371 of pending international application PCT/EP2018/061703 filed May 7, 2018, which claims priority to European Patent application EP 17169992.9, filed May 8, 2017, the entirety of which applications are hereby incorporated by reference herein.

The present invention relates to devices for use in heart surgery, more specifically to devices useful in reconstructive surgery of insufficient aortic valves and/or an aortic aneurysm repair.

When the medical diagnosis indicates an intolerable severity of the disease, the affected patient needs an operative correction. One of several options is the valve sparing root replacement. In this surgery, the aortic valve may be sewn into a vascular prosthesis that is implanted into the patient's body. This technique is also called re-implantation technique. Alternatively, a vascular prosthesis, which is also called graft, is connected to the patient's vessel along the valve, which is also called remodelling.

During the valve sparing root replacement the aorta of a patient is clamped and opened up. A graft with a first end and a second end is, at its first, open end, connected to the patient's vessel and/or heart. At this point of the surgery, the first end of the graft is a distal end of the graft and the second end is a proximal end of the graft. The connection may be made at the aortic root (e.g., the natural aortic root or an aortic neo root) and/or around the aortic valve, preferably with sutures. The second end of the graft is then connected to the other part of the opened vessel, preferably by sutures. After re-establishing the circulatory system of the patient the proper functionality of the valve and the graft may be verified.

Throughout the application, the terms proximal and distal are used for identifying locations along a device and/or a pathway from the point of view of a user performing the surgery and/or using an embodiment of the invention for other purposes. That is to say that something proximal is closer to a user than something distal. This may differ from other publications relating to vessels where the terms proximal and distal are used referring to the location with respect to the heart.

The techniques of valve sparing root replacement are constantly modified and improved. Nevertheless, these techniques still lack a possibility of verifying the correct fit and functionality of the heart valve as well as the leak tightness of one or more sutures of the graft to the one or more vessels. With the currently established technique, the medical personnel has to re-establish the circulatory system, before the medical personnel can actually verify the success of the surgery, i.e. verify that the valve is properly working and/or that all connections at the suture sites are leakproof. Consequently, if a leak occurs and/or the aortic valve does not work properly, another surgical correction has to be performed. This often includes clamping one or more affected vessels, improving the one or more sutures connecting the aortic graft to the one or more vessels, modifying or replacing the aortic valve, re-establishing the patient's circulatory system and/or verifying the success of the surgery. This is obviously stressful and potentially harmful for the patient and adds additional risks to the surgery procedure.

The present invention aims at overcoming these risks and problems. The invention is defined by the features of the claims.

The present invention relates to an aortic graft occluder. The aortic graft occluder may be a simple and effective device, for example, for use in the valve sparing root replacement. The aortic graft occluder may also be used in other surgical techniques, e.g. an abdominal aortic surgery. The aortic graft occluder may be used for intra-operative leak testing of a partially implanted tubular aortic graft, e.g. during valve sparing root replacement. Intra-operative leak testing may include verifying functionality of the heart valve, particularly its closing efficiency, as well as the leak tightness of one or more sutures of the graft to the one or more vessels. As such, the terms "leak tight", "leak tightness", "leak testing" and the like relate to (i) tightness of the system at least at the connection (suture) site of the aortic graft to the body of the patient or (ii) at the aortic valve (i.e., tightness of the closed valve) or (iii) both.

The aortic graft occluder is used with a corresponding graft having a first, distal end and a second, proximal end and a lumen connecting the first and second ends. Preferably, the first end comprises an opening and the second end comprises an opening. The aortic graft occluder is used to sealingly close a partially implanted aortic graft at its non-attached proximal end, before the graft's proximal end is connected to the patient's vessel, while the distal end of the graft has already been connected to the patient's vessel and/or heart. Simultaneously, the aortic graft occluder provides an access to the lumen of the graft. Via this access, the lumen of the graft may be filled with fluid, i.e. gas and/or liquid (e.g., saline). By filling the lumen of the graft with fluid and preferably by thereby pressurizing the interior of the graft, the leak tightness of the graft, specifically at its attachment site where it is typically sutured to tissue, may be verified. Additionally or alternatively, the aortic graft occluder may be used to pressurize the interior of the graft and simulate a diastolic blood pressure across the aortic valve. By simultaneously imaging the valve, e.g. by ultrasound, e.g. by applying a transesophageal ultrasound technique, the proper functionality (e.g., closing efficiency) of the valve may be verified during the surgery.

The aortic graft occluder may comprise a plug that may be configured for sealingly closing the opening of the proximal end of the aortic graft. Any graft that may be suitable for the above mentioned surgeries is contemplated. Common aortic grafts are available with nominal diameters of e.g. 26 mm, 28 mm, 30 mm or 32 mm. The size, especially the diameter, of the aortic graft occluder may be compatible with any of these diameters. For example, the plug may have a diameter corresponding to a nominal graft diameter of 26 mm, 28 mm, 30 mm and/or 32 mm. However, the currently common graft diameters are not limiting. The size, especially the diameter, of the aortic graft occluder may correspond to any desired diameter within the limits that are set by the anatomical limitations. Specifically, the aortic graft occluder may be adapted to grafts having a diameter of 8 mm to 45 mm.

The plug may comprise a first pathway. The plug with the first pathway is designed such that, when the plug is correctly attached to the proximal opening of the aortic graft, the first pathway is in fluid communication with the lumen of the aortic graft. The first pathway may be adapted for fluidly connecting to the lumen at a distal end of the pathway. Thus, when the aortic graft occluder is properly installed, the first pathway provides an access to the lumen of the graft through the plug that otherwise seals the lumen of the graft against the exterior of the graft. The first pathway may be further adapted for being connected with a feed line. The connection of the first pathway with the feed line may be located at a second, proximal end of the first pathway.

Via the feed line, fluid for insertion into the interior (i.e. the lumen) of the graft may be provided. Preferably, blood and/or physiological salt solution is/are used as said fluid. The fluid may be of a colour and/or comprise an additive being of a colour that is distinguishable from the patient's body and/or body compounds. This may facilitate the recognition of leaks for the user because coloured fluid leaking from the graft may be recognized much easier than blood or colourless fluid leaking from the graft. For example, the fluid may comprise methylene blue.

Preferably, the first pathway extends to a first connector, preferably a standardized connector, the connector being adapted for sealingly connecting with the feed line. The feed line may comprise a corresponding connector. The first, standardised connector may be a Luer type connector, preferably a Luer lock connector or a Luer slip type connector. Additionally or alternatively, the first connector may be any connector that allows a sealed transmission of fluid in a range from just above 0 bar to 0.6 bar.

The aortic graft occluder may comprise a second pathway. Thus, when the aortic graft occluder is properly installed, the second pathway provides an access to the lumen of the graft through the plug that otherwise seals the lumen of the graft against the exterior of the graft with the exception of the first pathway. A first end of the second pathway is adapted for being, preferably at a distal end of the second pathway, in fluid communication with the lumen of the aortic graft when correctly attached to the aortic graft. The second pathway may extend to a second connector, preferably a standardized connector, the second connector being preferably located at a second, proximal end of the second pathway. The standardized connector of the second pathway may be a Luer type connector, preferably a Luer lock connector or a Luer slip type connector. Additionally or alternatively, the connector of the second pathway may also be any connector that allows a sealed transmission of fluid in a range from just above 0 bar to 0.6 bar. The second connector may be of the same type as the first connector. Alternatively, the first connector and the second connector may differ from one another. In general, any connector type may be used with the first and second pathways. If the aortic graft occluder comprises more than one connector, the connectors may comprise differentiating marks, e.g. a colour code, a haptic code and/or a symbolic code, that may help differentiating the connectors and may thus facilitate the connection procedure.

The second pathway may serve as an outlet for any fluid, i.e. gas (e.g. air) and/or liquid, within the lumen of the graft by connecting the lumen of the graft with the exterior of the graft. Thus, when filling the lumen of the graft by inserting a fluid, e.g. physiological salt solution, any fluid in the lumen of the graft, specifically blood, excess physiological salt solution and/or gas such as air, may exit the graft via the second pathway. Preferably, any gas (e.g. air) contained in the graft is removed by continuously adding fluid to the graft's lumen via the first pathway, the added fluid ultimately replacing the gas in the lumen. The gas in the lumen may exit the lumen via the outlet, i.e. the second pathway. To aid the gas leave the lumen it is preferred that the aortic graft occluder and its second pathway is positioned at the highest point of the graft-aortic graft occluder-combination. Substantially complete removal of gas such as air from the graft is advantageous for the leak testing because working with substantially only an incompressible fluid ensures a physically defined situation during pressurization of the lumen of interest. Moreover, it is also beneficial for the testing of the aortic valve's functionality, e.g., the leak tightness of the closed valve, because this test may require imaging the aortic valve with transesophageal ultrasound. The technique of transesophageal ultrasound may also benefit from a gas free imaging environment.

A discharge line may be connected to the second pathway, preferably by means of the second connector and a corresponding connector of the discharge line. This may help to direct waste fluid exiting the graft to a proper location that is preferably at a safe location with respect to the patient's body. Moreover, the risk of body fluids accidentally entering the aortic graft occluder via the second pathway is reduced.

The flow through the second pathway may be regulated by any suitable means. Preferably, a plug or cap adapted for sealingly closing the second pathway is provided, thus inhibiting any flow through the second pathway. For example, the cap may comprise a thread that corresponds to a thread of the second pathway and/or the second connector, thus providing a sealing connection of the cap with the second pathway. More preferably, a discharge line with a valve is sealingly connected to the second pathway, preferably via the second connector. The valve may be manually and/or automatically controllable to open and/or close the discharge line and thus the second pathway. Any suitable valve is contemplated, e.g. any system that securely seals the second pathway in a pressure range of just above 0 bar to 0.6 bar, e.g. a 1-way stopcock and/or a 2-way stopcock, which may include a Luer type connector and/or a clip as known from central venous catheters.

The plug of the aortic graft occluder may be adapted to be at least partially inserted into the lumen of the graft. The plug may be adapted to be removably, preferably tool-free removably, connected to the graft. The plug may comprise a sealing section adapted for providing a leakproof connection between the plug and the graft. The sealing section is also called sealing region. Preferably, a sealing ring with an appropriate cross section, preferably a circular cross section, is included. The sealing ring may be an O-ring seal or any other type of sealing ring. The sealing section and preferably the sealing ring may comprise any material that facilitates sealing of the plug against the aortic graft. The sealing ring is preferably attached to the plug in a way that impedes a tool-free removal of the sealing ring from the plug. The attachment of the sealing ring to the plug may be realized with any suitable means, e.g. clamping, clipping, bonding, tacking, screwing and/or sewing and/or any combination thereof.

Many aortic grafts used in the art have a threaded wall structure. The aortic graft occluder may thus comprise a corresponding thread. Preferably, the thread of the aortic graft occluder is located on the plug. The corresponding threads of the graft and the aortic graft occluder may be used to connect the aortic graft occluder with the graft. Preferably, this is a sealing, i.e. leakproof, connection.

Different types of grafts may comprise different diameters (as indicated above) and/or different types of threads. It is contemplated that the aortic graft occluder has a diameter and a thread that correspond to the thread of the graft that is used in the respective surgery. For example, the threading of the graft may be present on the interior surface of a wall of the graft. The corresponding aortic graft occluder may comprise an external thread, preferably located on the plug, adapted to be screwed into the internal threading at the proximal end of the graft. Additionally or alternatively, the wall of the graft may comprise a threading on its exterior surface. The corresponding aortic graft occluder may comprise an internal thread adapted to be screwed onto the external threading of the proximal end of the graft. Preferably, the internal thread of the aortic graft occluder is located at the plug. An aortic graft occluder may comprise different types of threads. For example, an aortic graft occluder may comprise a first, exterior thread with a first diameter and a second, exterior or interior thread with a second diameter. Exterior and interior threads are also called external and internal threads, respectively. Such a double threaded plug may be advantageous because it may be connected to different grafts with threads of different diameters and/or different types, thus reducing the number of devices that have to be available during a surgery.

The aortic graft occluder may include an extension extending from the plug. The first pathway and/or the second pathway and/or any further pathway may extend through the extension. Within the extension, the first, second and/or any further pathways may extend separated from one another. Additionally or alternatively, each pathway may extend through a different extension. Preferably, the extension includes the first and/or second and/or any further connectors, preferably at an end opposite the plug, which is preferably a proximal end of the extension. The extension may be configured to remain at least partially outside of the lumen of the aortic graft when the aortic graft occluder is attached to the graft. Preferably, at least 10 mm, more preferably at least 20 mm, more preferably at least 30 mm and most preferably at least 40 mm of the length of the extension remain outside the lumen of the graft. However, it is also contemplated that a larger portion of the extension remains outside the lumen of the graft. This may help to improve the handling of the device during the surgery. For instance, this design may facilitate the connection of the feed line to the aortic graft occluder during surgery.

The extension may include a rigid and/or a flexible region. For example, it may comprise a flexible tube. The first pathway and the second pathway may at least partially extend through the flexible tube. Preferably, the extension comprises a first flexible tube at least partially comprising the first pathway and a second flexible tube at least partially comprising the second pathway. The one or more flexible regions, preferably the one or more flexible tubes, may be located between the one or more connectors and the plug. This design improves the flexibility of the device, thus, e.g., facilitating the procedure of connecting the one or more pathways to the feed line and/or the discharge line during a surgery. The extension may additionally or alternatively comprise a rigid region. The rigid region may extend from the plug to the one or more connectors, the plug preferably being located at a first, preferably distal end of the rigid region and the connector(s) preferably being located at a second, preferably proximal end of the rigid region.

The aortic graft occluder may comprise a locking means. When the plug is at least partially inserted into the lumen of the graft, e.g., by screwing a threaded plug into the threaded wall of a graft, the locking means may press a portion of the graft that extends over a portion of the aortic graft occluder at least partially against the plug, preferably thereby sealingly connecting the aortic graft occluder with the graft. Preferably, the locking means presses the portion of the graft at least partially against the sealing section, preferably against the sealing ring. Preferably, the portion of the graft that is at least partially pressed against the plug is a proximal portion of the graft. Preferably, this is reversible, i.e. the locking means may preferably be removed, thereby loosening the seal.

The extension may comprise an external thread, whereas the locking means may comprise an internal thread matching the external thread of the extension. The locking means may be configured to be driven, with its internal thread, along the external thread of the extension. A progressive screwing of the locking means along the extension may cause that at least the, preferably proximal, portion of the graft that extends over a portion of the aortic graft is at least partially pressed against the sealing section, thus providing a seal, i.e. leakproof, connection of the plug with the graft. A gradual sealing may be caused by the locking means having an internal, tapered section. When the tapered locking means is driven along the external thread of the extension, the internal tapered section progressively presses at least a, preferably proximal, portion of the graft at least partially against the plug, preferably against the sealing section. Due to the internal tapering of the locking means, progressively screwing the locking means along the extension causes a gradual increase of pressure on the graft portion that is pressed against the plug, ultimately resulting in a sealing, i.e. leakproof, connection of the plug with the graft. The tapering may have any suitable shape, e.g. may be straight tapered, stepwise tapered and/or curved tapered.

In a preferred embodiment, the locking means may be secured to the plug and/or the extension of the aortic graft occluder so as to form a unit for use. The locking means may nevertheless be removable, preferably tool-free removable, from the plug and/or the extension. For example, the locking means may have an annular shape with an internal thread. The opening in the annular shaped locking means and the remainder of the aortic graft occluder are designed such that the locking means may only be slipped over and/or off the plug and/or the extension of the aortic graft occluder when the aortic graft occluder and the locking means are oriented in a certain relative orientation. In this way, it is possible that the locking means is intentionally slipped on and/or off the aortic graft occluder, while an accidental removal of the locking means form the aortic graft occluder is largely hampered or (almost) impossible. This may improve the handling of the device and may provide additional security by preventing an accidental loss of the locking means, e.g., in the body of the patient during surgery.

The locking means may further comprise a structured region that provides sufficient grip to, preferably gloved, fingers of a user to securely hold the locking means and to securely use and install the locking means. The structured region may be located at any suitable location, depending on the exact shape of the aortic graft occluder and the locking means. For example, the structured region may be located at a proximal edge of the locking means. The structured region may comprise concavities and convexities of any kind, e.g., riffles, to provide the increased friction.

In an embodiment, the aortic graft occluder may comprise a plug with a circumferential notch or groove. The plug is preferably substantially cylindrically shaped. The length of the plug is not particularly limited. However, it is preferred that it has a length of 5 mm or more, preferably 8 mm or more, more preferably 12 mm or more and most preferably 15 mm or more. Preferably, the notch extends on the side wall of the cylinder, preferably substantially parallel to a shortest circumference of the cylinder. The notch or groove may have any suitable cross-sectional shape, preferably semi-circular, partially elliptical, V-shaped, U-shaped, partially straight, partially rectangular, partially trapezoidal and/or partially polygonal.

The aortic graft occluder comprising the circumferential notch may be removably attached to the graft with the aid of a locking means. Preferably, the corresponding locking means comprises a ligature, a filament, a wire and/or a string of any suitable type. Preferably the corresponding locking means is a sling. The ligature, the filament, the wire and/or the string may be made from any suitable material, e.g., polyamide, polyester, polyglactin, polyglycoacid, polypropylene, ultra high molecular polyethylene (UHMPE). The aortic graft occluder comprising the notch or groove may be configured to be inserted into the graft with the notch running substantially along the interior surface of the wall of the graft. The corresponding locking means is preferably configured to be wound around the exterior of the graft and tightened such that the locking means presses a portion of the wall of the graft into the notch of the aortic graft occlude, preferably thereby sealingly connecting the aortic graft occluder with the graft. The notch may thus serve as the sealing section. The locking means may comprise a means for removably fixing the sling in the tightened position, e.g., stoppers of any type. Additionally or alternatively, the locking means may be kept in the tightened position by fastening it with one or more knots.

The aortic graft occluder may comprise one or a combination of biocompatible, preferably medical, materials. Preferably, the aortic graft occluder may comprise an alloy of titanium and/or stainless steel. Additionally or alternatively, the aortic graft occluder may comprise biocompatible, preferably medical, synthetics, for example polyphenylene sulfide (PPS), polystyrene (PS), polyoxymethylene (POM) and/or polyether ether ketone (PEEK). The aortic graft occluder may consist of one or a combination of these materials.

The aortic graft occluder may be configured to provide the fluid-tight connection with the graft for an intraluminal pressure of at least 70 mmHg, preferably at least 80 mmHg, more preferably at least 90 mmHg, more preferably at least 100 mmHg, more preferably at least 150 mmHg, more preferably at least 200 mmHg and most preferably at least 250 mmHg. The resistance of the installed system to said pressures not only enables testing of the aortic valve functionality (e.g., valve closure) and leak tightness of the graft suture(s) during surgery. By providing a pressure resistance that exceeds the physiologically reasonable pressures, it may also be used in ex vivo applications, e.g. leak tightness tests. However, the aortic graft occluder may alternatively comprise a predetermined breaking point that yields under a predefined pressure, e.g., 250 mmHg and preferably 200 mmHg, thus providing an additional security mechanism that impedes the application of e.g. physiologically critical pressures during an intraoperative test.

The aortic graft occluder may also comprise a third pathway. The third pathway may extend through the aortic graft occluder and be configured to provide an access to the lumen, when the aortic graft occluder is installed on the graft. The third pathway may be adapted for serving as an inlet for introducing a medical device, e.g., a probe, a catheter, a cannula such as a cannula used with a heart-lung apparatus and/or any other required device, through the installed aortic graft occluder into the otherwise sealed lumen of the graft. The inlet, i.e. the third pathway, may be adapted to the device that is intended to be inserted through the third pathway. The third pathway may comprise a sealing mechanism against the exterior that is configured to sealingly close the third pathway when the device, such as a probe and/or a catheter, is inserted and properly connected. For example, the third pathway and the device may comprise corresponding threads that are configured to sealingly connect the device with the third pathway. The aortic graft occluder may comprise a cover or cap that may be attached to the third pathway when no additional device is inserted into the third pathway. The cover or cap is adapted to sealingly close the third pathway. The cover or cap may comprise a sealing section, e.g., a sealing ring, preferably an O-ring seal. Additionally or alternatively, the cover or cap may comprise a thread that matches a thread of the third pathway, for sealingly screwing the cover or cap into and/or onto the third pathway.

In an embodiment, an echo probe for 3D-imaging of the aortic root under pressure may be inserted via the third pathway.

Additionally or alternatively, the aortic graft occluder may have a second pathway comprising the features described in connection with the third pathway.

In an embodiment of the invention, the aortic graft occluder and the graft are designed as a unit. In such an embodiment, a first end of the graft is open and configured for being connected to a vessel, the first end thus being the distal end of the graft. In this embodiment, the graft has a proximal end being closed by the plug of the aortic graft occluder, for example, as described above. Alternatively, the plug may also be fixed to the graft in any suitable way, e.g. by sewing, gluing, welding, crimping, melting, and the like. The graft may also have a closed end as a result of the aortic graft occluder being integrally formed with the graft. For example, the plug may be integrally formed with the graft. After the connection of the graft to the vessel, a leak test may be performed. In case of leakage, the connection of the graft to the vessel may be corrected and again tested. In case of leak tightness, the proximal end of the graft comprising the aortic graft occluder may be cut, clipped, ripped off or otherwise disconnected and the thus created free end of the graft may be positioned and stitched to the appropriate site in the patient's body.

In an embodiment of the aortic graft occluder, one or any combination of the plug, the one or more extensions and the one or more connectors may be integrally formed.

For the verification of the functionality of the aortic graft occluder it may be desirable to run a test in which the aortic graft occluder is connected to a graft and the connection is tested for its leak tightness. In accordance with the testing method, the aortic graft occluder according to the invention is connected to one end of a graft to be used. The other end of the graft is closed with any suitable plugging means. The first pathway of the aortic graft occluder is connected to a fluid reservoir. The aortic graft occluder may be connected to the fluid reservoir via a feed line. However, the feed line may itself be the fluid reservoir or at least a part of it. If the aortic graft occluder comprises a standardized connector, the aortic graft occluder is preferably connected, via the connector, to the feed line. All connections are configured to withstand the pressures that are intended to be applied. For example, Luer type connectors may be used for a huge range of pressures, as is well known in the art. However, the type of connection to the fluid reservoir is not limiting. Fluid from the reservoir may then be inserted into the graft via the first pathway, preferably via the feed line. This may be achieved by any suitable means, e.g., by a manually operated pump such as a syringe, an elastic tubular body and/or by an automatic pump, e.g., a peristaltic pump or a vibrating diaphragm pump. The applied pressure, as created by inserting the fluid into the graft, is measured with a properly installed and suitable pressure sensor. The measuring position is not limiting, and may be chosen in accordance with the used sensor, preferably taking into account the dimensions and the shape of the setup. Preferably, pressures up to at least 70 mmHg, preferably at least 80 mmHg, more preferably at least 90 mmHg, more preferably at least 100 mmHg, more preferably at least 150 mmHg, more preferably at least 200 mmHg, most preferably at least 250 mmHg are applied.

Although it is possible to apply and measure a pressure with gas, e.g. air, trapped in the graft, it is preferable to remove any trapped air (or any other gas) from the graft before measuring a pressure. This may facilitate accurate pressure measuring. If a second pathway serving as an outlet is present, the outlet is set to an open state when filling the graft with fluid, allowing trapped gas (e.g. air) to escape through the outlet, when the space in the lumen is filled up with the fluid. In order to support this gas removal process, it may be recommendable to orient the setup in a way that the second pathway is the highest point of the aortic graft occluder and graft. With such an orientation, the graft is substantially free of trapped air or other gas, when fluid starts to exit the outlet. The second pathway (i.e. the outlet) is then sealingly closed, preferably by closing a suitable valve attached to the second pathway, by adding a lid or cap to the second pathway of the aortic graft occluder and/or by any other means. Pressure may then be applied, e.g., as described above. If the aortic graft occluder comprises a third pathway, the third pathway is preferably kept sealingly closed throughout the procedure. The same may apply for any further pathway the aortic graft occluder may comprise.

It has been found for embodiments of the present invention to maintain leak tightness with intraluminal pressures that amount to, e.g., twice the biologically relevant pressures of, e.g., at least 250 mmHg over a testing period of up to 20 minutes.

Further, a method for leak testing of a tubular aortic graft having a distal end attached to an aortic root and having a free, proximal end by means of the aortic graft occluder in accordance with the invention will now be described. The method may be applied between two consecutive steps of a surgery, e.g., a valve sparing root replacement. The method comprises the step of sealingly attaching the aortic graft occluder to the free, proximal end of the graft. After having established a leakproof connection of the aortic graft occluder with the graft, the lumen of the graft is separated from the exterior of the graft except for the one or more pathways provided by the aortic graft occluder and, if present, leaks. The method further comprises the step of connecting the lumen of the aortic graft with a feed line by connecting the first pathway of the aortic graft occluder to the feed line, preferably via a standardized connector of the aortic graft occluder and a corresponding connector of the feed line, wherein the feed line is configured to provide fluid to the first pathway. Preferably, the feed line is in turn connected to a fluid reservoir of sufficient volume, e.g., an infusion bag of, e.g., physiological salt solution. Fluid may be inserted into the lumen of the graft via the first pathway, preferably via the feed line. This may be achieved by any suitable means, e.g., by a manually operated pump such as a syringe, an elastic tubular body and/or by an automatic pump, e.g., a peristaltic pump or a vibrating diaphragm pump. The intraluminal pressure that is thereby applied to the graft is measured with a suitable pressure sensor. The measuring position is not limiting, and may be chosen in accordance with the used sensor, preferably taking into account the dimensions and the shape of the setup. By continually measuring and checking the pressure in the graft physiologically critical pressures may be avoided. The pressure in the graft is preferably set to be above atmospheric pressure, preferably to at least 70 mmHg, preferably at least 80 mmHg, more preferably at least 90 mmHg, more preferably at least 100 mmHg, more preferably at least 150 mmHg, more preferably at least 200 mmHg and most preferably at least 250 mmHg, but always within the limits as set by the involved biological system.

Although it is possible to apply and measure a pressure with gas, e.g. air, trapped in the graft, it is preferable to remove any trapped gas from the graft before measuring a pressure. This may facilitate accurate pressure measuring. If a second pathway serving as an outlet is present, the outlet is set to an open state when filling the graft with fluid, allowing trapped gas to escape through the outlet, when the space in the lumen is filled up with the fluid. In order to support this gas removal process, it may be advantageous to orient the setup in a way that the second pathway is the highest point of the aortic graft occluder and graft. With such an orientation, the graft is substantially free of trapped gas, e.g. air, when fluid starts to exit the outlet. The second pathway (i.e. the outlet) is then preferably sealingly closed, e.g., by adding a lid or cap to the second pathway of the aortic graft occluder and/or by any other means, e.g., by closing a suitable valve attached to the second pathway. Pressure may then be applied, e.g., as described above. If the aortic graft occluder comprises a third pathway, the third pathway is preferably kept sealingly closed throughout the procedure. The third pathway may also be kept open during and for supporting the gas removal process, e.g. by allowing air to exit the lumen. The same may apply for any further pathway the aortic graft occluder may comprise. The method may further comprise the step of checking the attachment of the distal end of the aortic graft to the aortic root for leak tightness by checking for fluid leaking from the attachment. A leak may be identified through the leakage of fluid from the connection of the graft to the aortic root, the fluid being preferably of a colour that is easily distinguishable from a human body. Additionally or alternatively, leak testing of the aortic graft occluder may comprise pressurizing the interior of the graft and simulating a diastolic blood pressure across the aortic valve. By simultaneously imaging the valve, e.g. by ultrasound, proper functionality (e.g., closing efficiency (tightness)) of the valve may be verified during the surgery.

Experiments with the aortic graft occluder of the present invention have shown that the use of the occluder allows for efficient and clinically meaningful verification of the functionality of aortic valves. The experiments were conducted as follows:

Introduction:

In case of aortic valve insufficiency, the regurgitating (blood-) volume can easily be detected by Color Doppler echocardiography. It appears as a colored jet with specific characteristics, such as size, volume, direction, origin and shape. Based on these facts a surgeon is able to draw conclusions on the valve's underlying pathology and therefore derive a proper surgical intervention.

Method:

The inventors' hypothesis was that the morphology of a dynamic jet and of a static jet are comparable, for the same simulated pathologies of a respective valve. An in vitro experiment was performed using a beating heart simulator with 15 porcine hearts. After anastomosis of a supra-commissural Dacron graft, the aortic valves were investigated during dynamic (beating) and static conditions, using the aortic graft occluder of the present invention at two pressure levels, 45 mmHg and 60 mmHg, respectively. Different jets have been generated by modification of the native valves. The characterizations of the jets were executed, using a clinical relevant ultrasound imaging technique.

Results:

Within the 15 porcine hearts a total of 108 paired studies (dynamic vs. static) were performed. At a root pressure of 45 mmHg, an identical result regarding a jet's existence, direction and orientation was observed in 50 out of 54 cases (92.6%). At a pressure of 60 mmHg, the accordance was even higher with 52 out of 54 (96.3%) matched pairs.

Conclusion:

These results indicate that, in static condition using the aortic graft occluder of the present invention, the sonographic appearance of a specific valvular regurgitation jet is highly comparable to the sonographic appearance of the beating heart.

After the leakage test, the aortic graft occluder may be removed from the graft. The surgery may then be continued.

The invention will be further explained by referring to the figures. It is noted that the figures serve to explain certain features that may be optional to the invention. The figures are not to be interpreted in a limiting way and any of the features discussed by referring to the figures may occur, alone or in combination with one or more other features, in other embodiments.

Figure 1A:
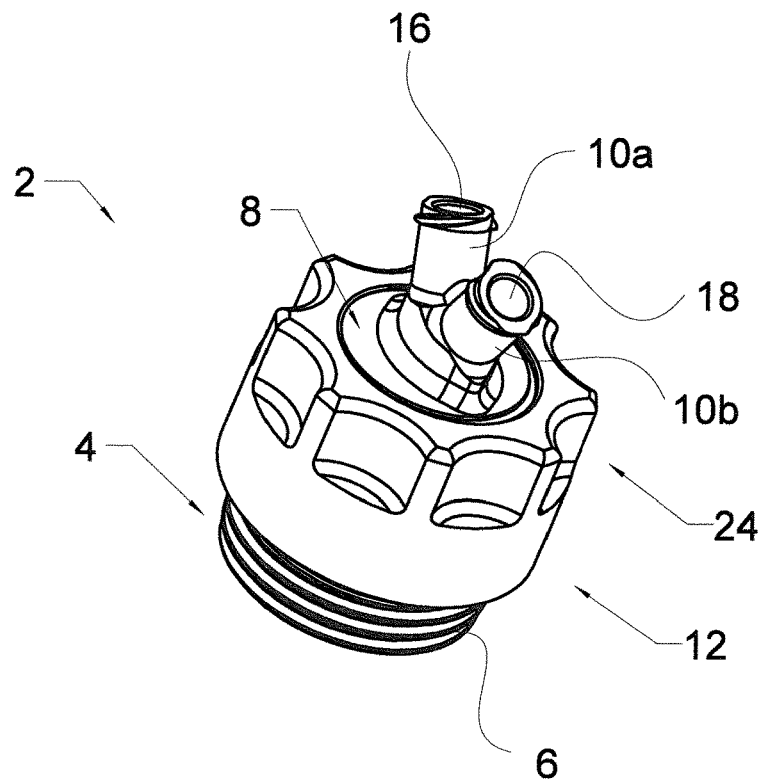
FIG. 1A shows an embodiment of the aortic graft occluder according to the invention in a perspective view.
Figure 1B:
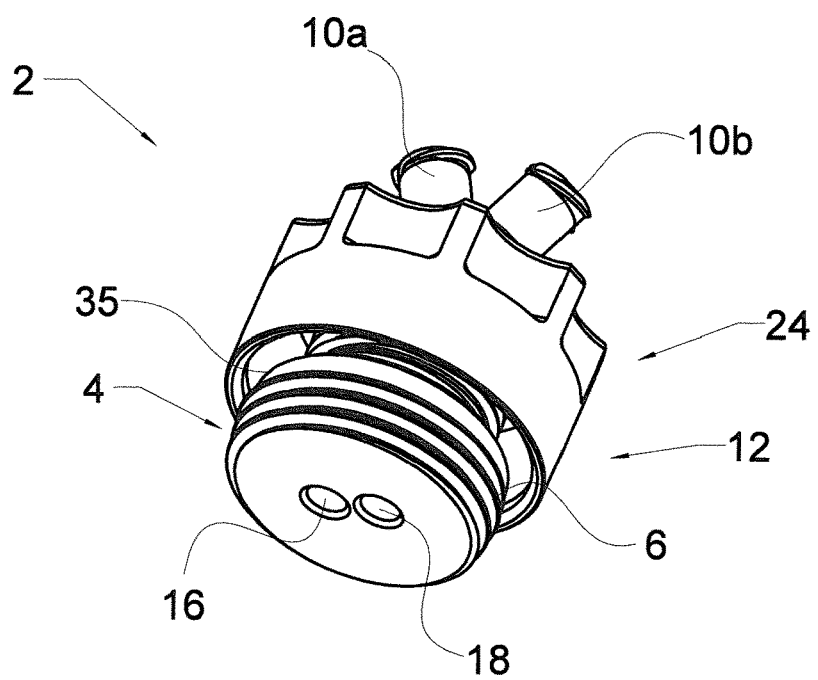
FIG. 1B shows an embodiment of the aortic graft occluder according to the invention in another perspective view.

FIG. 1A shows an embodiment of an aortic graft occluder 2 according to the invention. The aortic graft occluder 2 is shown in a perspective view in an angle from above. FIG. 1B shows the same embodiment in a perspective view in an angle from below.

The aortic graft occluder 2 may comprise a plug 4 with an external thread 6, as shown in FIGS. 1A and 1B. The plug 4 may comprise an extension 8 with two standardized connectors 10a, 10b, preferably Luer type connectors, more preferably Luer locks. The aortic graft occluder 2 may further comprise a locking means 12. The locking means 12 in the shown embodiment has an annular shape and is adapted for forming a functional unit with the plug 4 and its extension 8. The shown locking means 12 comprises an opening 14 that is adapted to the shape of the plug 4, the extension 8 and the connectors 10a, 10b in a way that the locking means 12 may be slipped into the depicted position, e.g., by conducting the locking means 12 along a particular way and/or in one or more particular orientations relative to the plug 4, the extension 8 and/or the connectors 10a, 10b. This ensures that the probability for the locking means 12 falling off the plug 4, which might result in accidental loss of the locking means 12, is significantly reduced. As indicated above, this may improve the handling by avoiding an accidental loss of the locking means 12, e.g., in the body of the patient during a surgery procedure which increases the security of the patient.

Figure 2A:
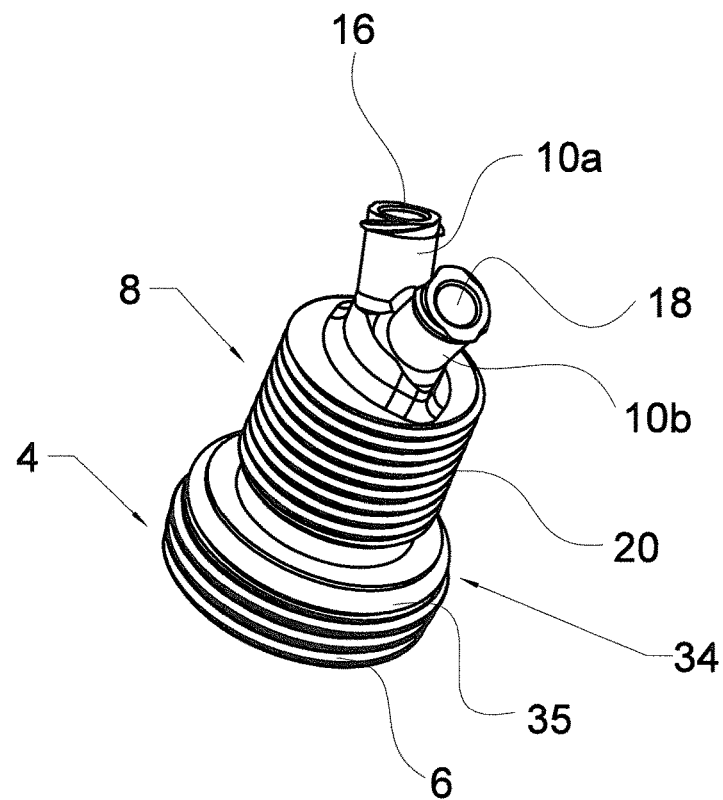
FIG. 2A shows a part of an embodiment of the aortic graft occluder according to the invention in a perspective view.
Figure 2B:
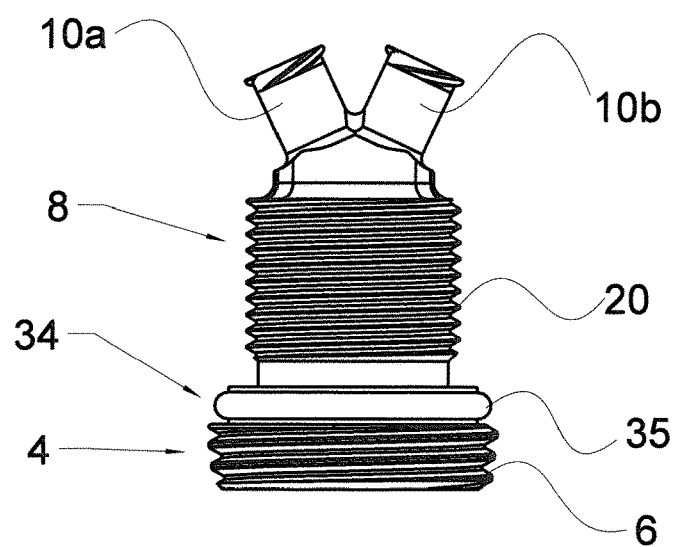
FIG. 2B shows the part of the aortic graft occluder of FIG. 2A in a side view.
Figure 2C:
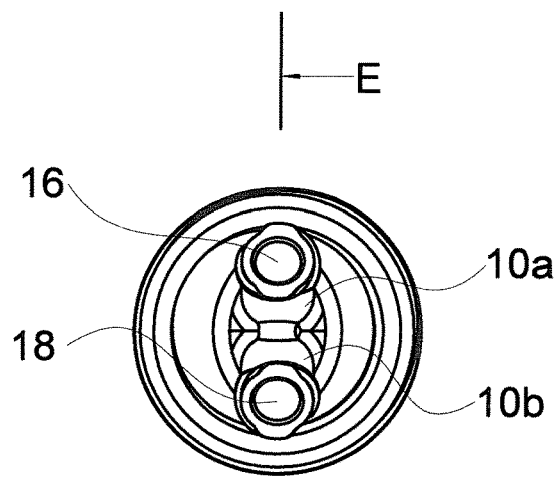
FIG. 2C shows the part of the aortic graft occluder of FIG. 2A in a top view.
Figure 2D:
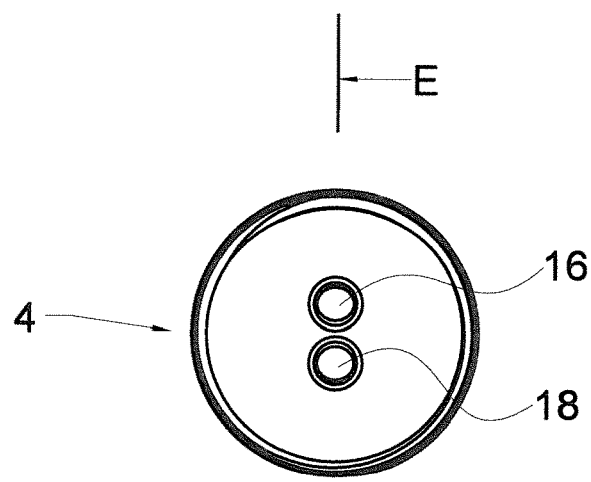
FIG. 2D shows the part of the aortic graft occluder of FIG. 2A in a bottom view.
Figure 2E:
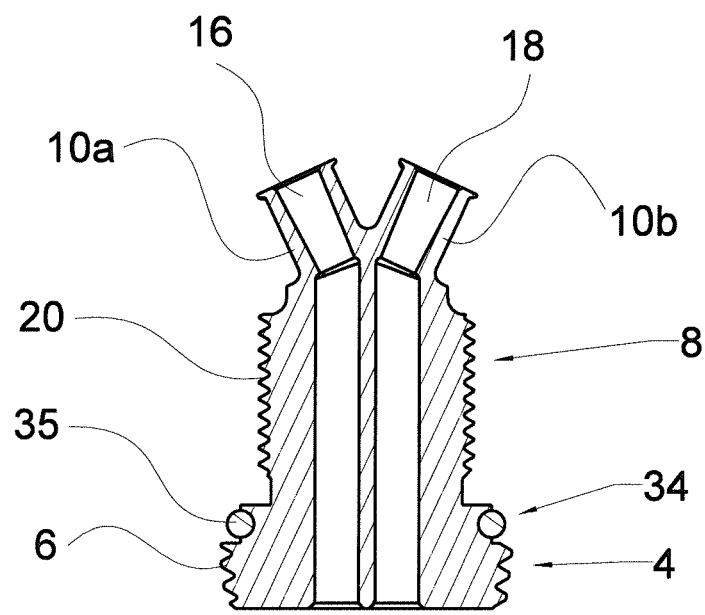
FIG. 2E shows a section of the part of the aortic graft occluder of FIGS. 2A-D as indicated by the line E-E in FIGS. 2C and 2D.

FIGS. 2A, 2B, 2C and 2D show the plug 4 of FIGS. 1A and 1B with its extension 8 and connectors 10a, 10b in a perspective view at an angle from above, a side view, a top view and a bottom view, respectively. A cross-section of the plug 4, extension 8, connectors 10a, 10b, as indicated by the line E-E in FIGS. 2C and 2D, is shown in FIG. 2E. FIGS. 2A 2E show that the aortic graft occluder 2 may have a first pathway 16 and a second pathway 18. The first pathway 16 extends from the first standardized connector 10a through the plug 4 and its extension 8. The second pathway 18 extends from the second standardized connector 10b through the plug 4 and its extension 8. First and second pathways 16 and 18 are, within the shown embodiment of the aortic graft occluder 2, fluidly separated from one another.

Figure 3A:
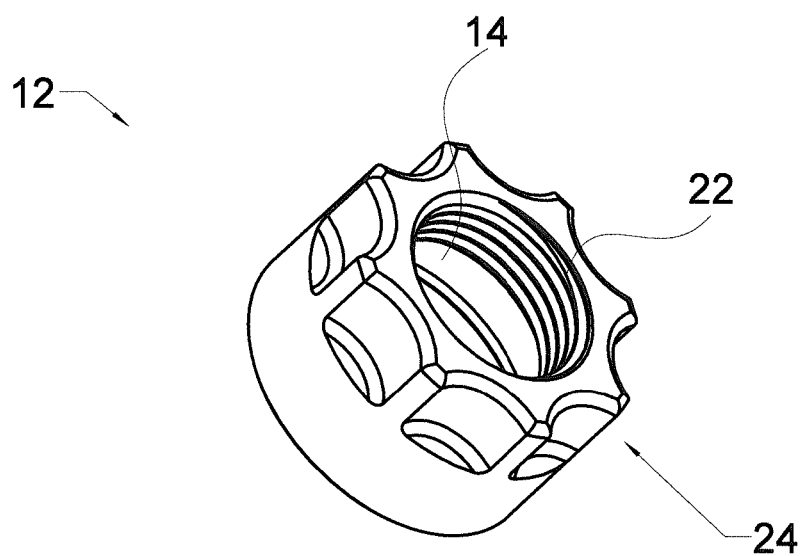
FIG. 3A shows an embodiment of another part of the aortic graft occluder according to the invention in a perspective view.
Figure 3B:
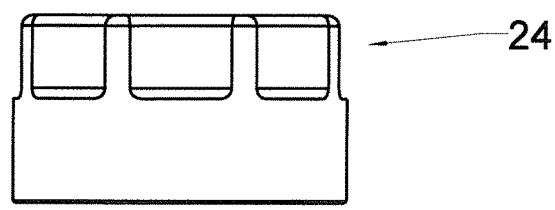
FIG. 3B shows the part of the aortic graft occluder of FIG. 3A in a side view.
Figure 3C:
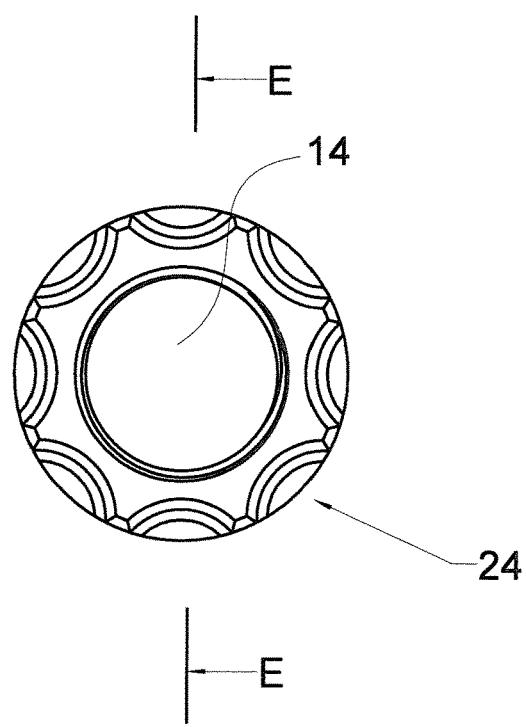
FIG. 3C shows the part of the aortic graft occluder of FIG. 3A in a top view.

FIGS. 3A, 3B, 3C and 3D show the locking means 12 of FIGS. 1A and 1B in a perspective view at an angle from above, in a side view, in a top view and in a bottom view, respectively. FIG. 3E shows a cross-section of the locking means 12 as indicated by the line E-E in FIGS. 3C and 3D. FIGS. 3A 3E show that the locking means 12 may have an annular shape. As shown, an interior thread 22 may be provided in an opening 14 of the locking means 12. The interior thread 22 that may also be described as being located on an interior wall of the locking means 12 may correspond to an external thread 20 of the extension 8. Thread 20 can be seen, e.g., in FIG. 2E. The locking means 12 may further comprise a structured region 24 that provides additional friction to, preferably gloved, fingers of a user. In the embodiment shown in FIG. 3E, the structured region 24 is located at the proximal edge of the locking means 12 and may comprise concavities and convexities of any kind, e.g. riffles.

Figure 3D:
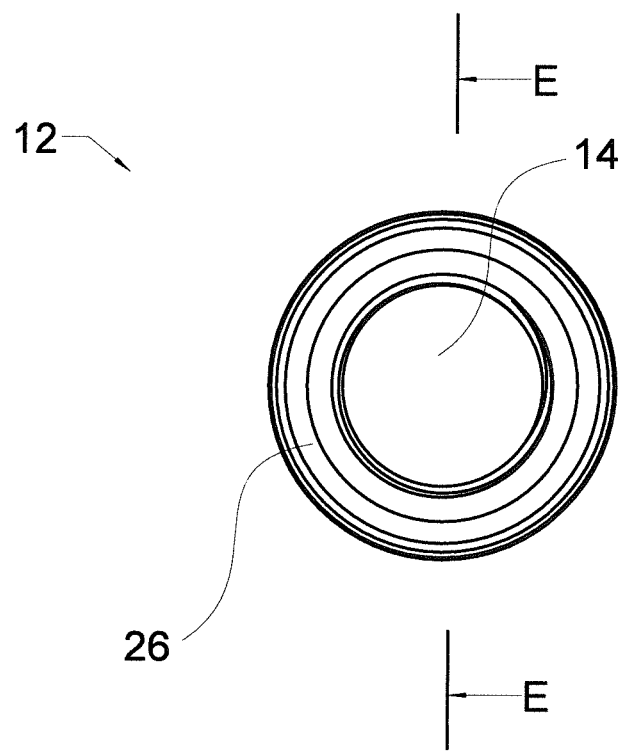
FIG. 3D shows the part of the aortic graft occluder of FIG. 3A in a bottom view.
Figure 3E:
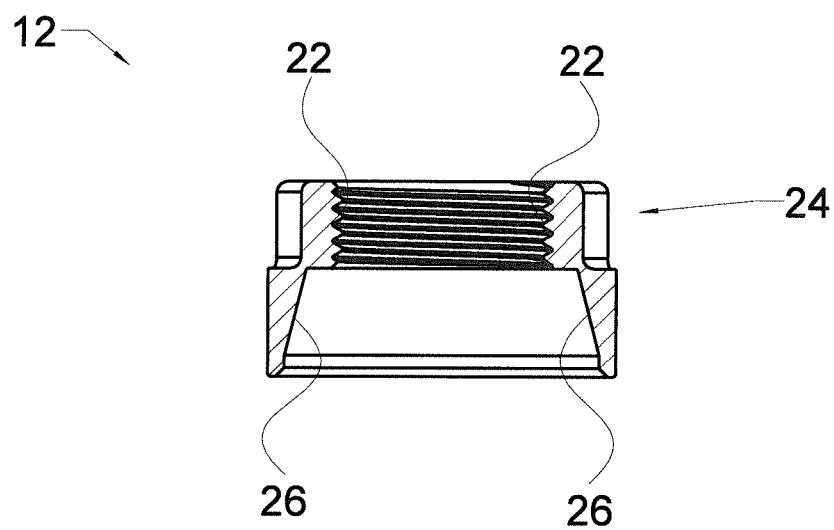
FIG. 3E shows a section of the part of the aortic graft occluder of FIGS. 3A-D as indicated by the line E-E in FIGS. 3C and 3D.

FIGS. 3D and 3E further show a tapered section 26. The tapered section 26 may be located at a distal end of the locking means 12, as can be seen in FIGS. 3D and 3E.

Figure 4A:
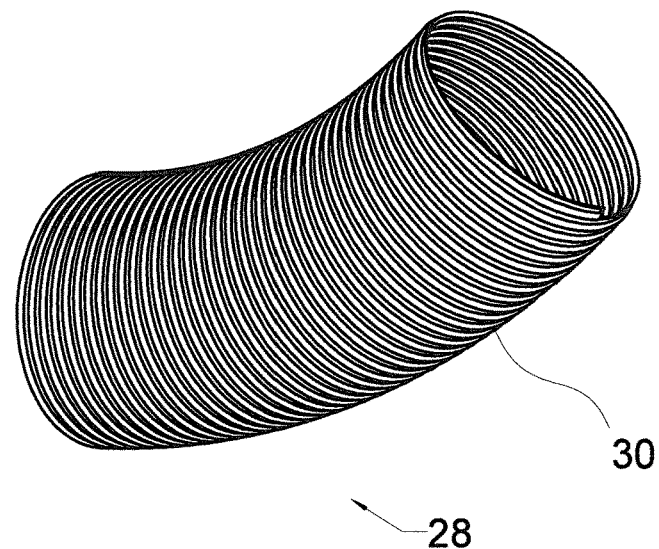
FIG. 4A shows a perspective view of an embodiment of a graft.

FIG. 4A shows a schematic drawing of an exemplary graft 28 used in valve sparing root replacement. The graft 28 may comprise a threaded structure 30 along its entire length, e.g.

in the form of a helical support element. Alternatively, the graft 28 may include a thread 30 at the graft's proximal end, wherein the thread 30 extends only over a portion of the graft 28.

The threaded structure of graft 28 may be realized on the internal surface as well as on the external surface of the graft 28, as depicted in FIG. 4A.

Figure 4B:
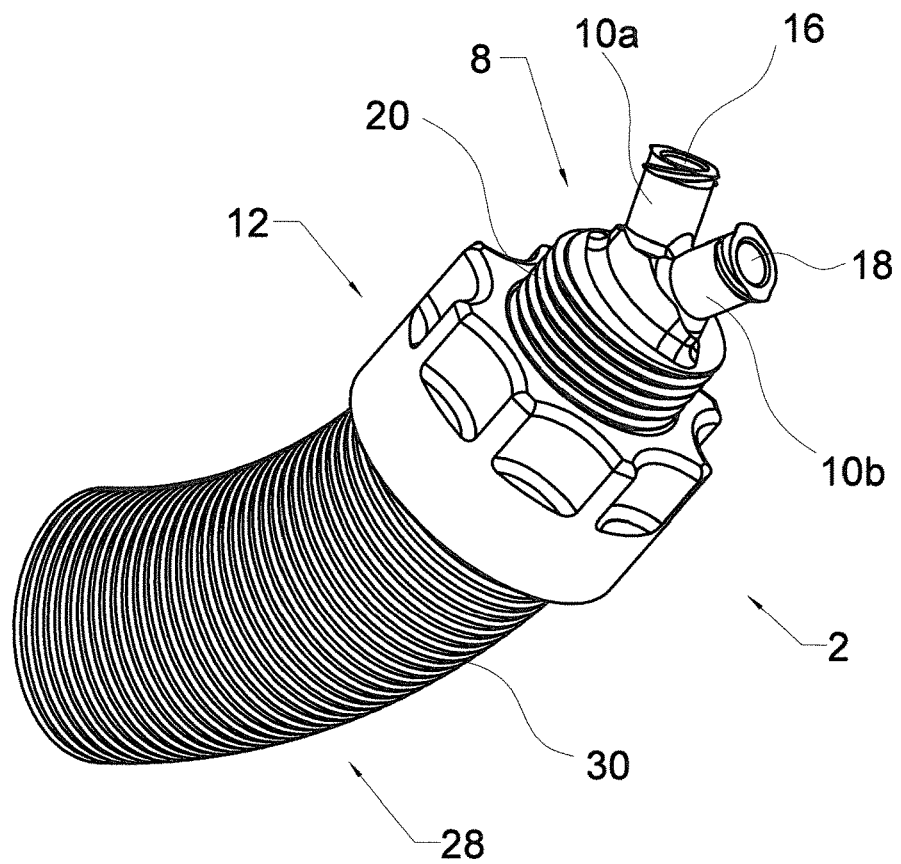
FIG. 4B shows a perspective view of the embodiment of the aortic graft occluder of FIGS. 1A and 1B attached to the graft of FIG. 4A.
Figure 4C:
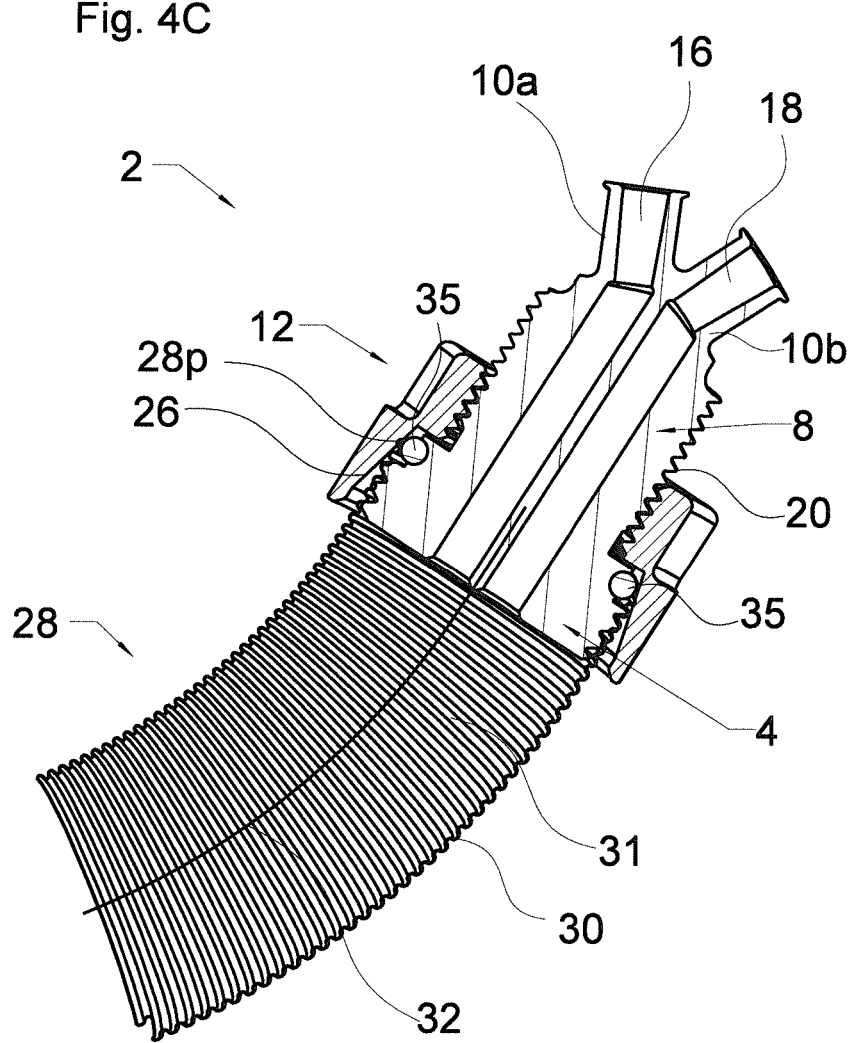
FIG. 4C shows a longitudinal cross section through the device of FIG. 4B.

FIG. 4B shows the embodiment of the aortic graft occluder 2 of FIGS. 1A-3E attached to the graft 28 of FIG. 4A in accordance with the invention. In FIG. 4B, the aortic graft occluder 2 is attached to the proximal end of the graft 28. In the situation of FIG. 4B, the aortic graft occluder 2 has been partially driven into the graft 28. More specifically, as shown in the corresponding cross-section in FIG. 4C, the plug 4 and a distal portion of the extension 8 have been driven into the lumen 31 of the graft 28. For example, a proximal portion 28p of the graft 28 (also referred to as proximal graft portion 28p) envelops at least a portion of the the plug 4 and optionally the distal portion of the extension 8. In the situation shown in FIGS. 4B and 4C, the locking means 12 has been slipped over the extension and driven distally along the graft 28 using the thread 22 of the locking means 12 and the thread 20 of the extension 8. The distal movement of the locking means 12 along the graft 28 causes the proximal graft portion 28p being at least partially pushed towards a longitudinal central axis 32 of the graft 28 by the tapered internal surface 26 of the locking means 12. As can be seen from FIGS. 2E, 3E and 4C, the plug 4 may comprise a sealing region 34. In the shown embodiment, the sealing region 34 may comprise a sealing ring 35, more specifically an O-ring with a circular cross-section. The sealing ring 35 may be attached to the plug 4 in a way that impedes a tool-free removal of the sealing ring 35 from the plug 4. The attachment of the sealing ring 35 to the plug 4 may be effected with any suitable means, e.g., clamping, clipping, bonding, tacking, screwing and/or sewing and/or any combination thereof. FIG. 4C shows that the tapered interior surface 26 of the locking means 12 presses at least a part of the proximal portion 28p of the graft 28 enveloping the plug 4 against the seal region 34, i.e. against the sealing ring 35, when screwed in a distal direction along the thread 20 of the extension 8. Here, pressure on at least part of the proximal graft portion 28p, as provided by the tapered region 26 of the locking means and the seal region 34 of the plug 4, increases with the locking means being driven further in a distal direction. It is to be understood that the shown straight shape of the tapered region 26 is not limiting and any other suitable shape, e.g., a curved and/or a stepwise instead of a straight tapering, is contemplated.

Figure 5:
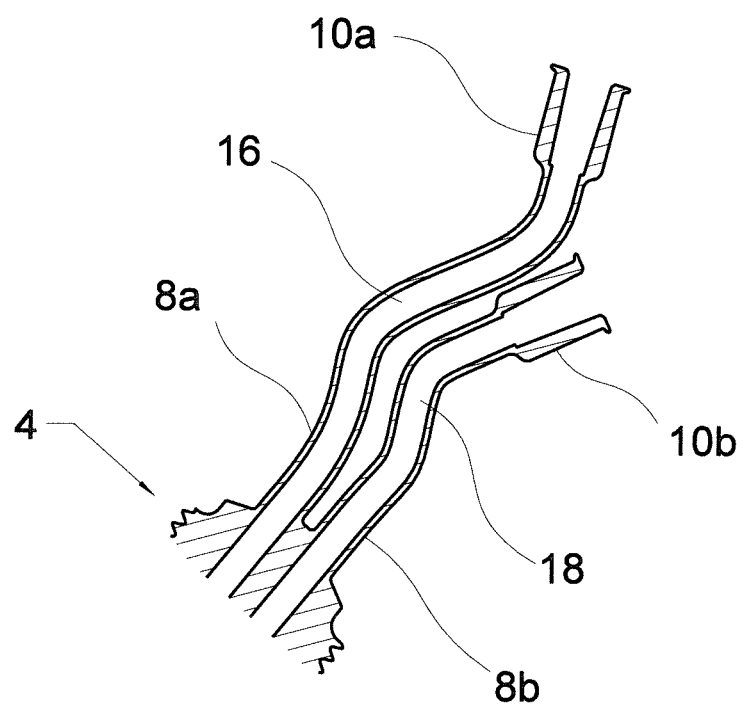
FIG. 5 shows a detail of another embodiment of an aortic graft occluder according to the invention in a cross section.

FIG. 5 shows a schematic drawing of a detail of an embodiment of an aortic graft occluder 2. The embodiment of FIG. 5 comprises a first extension 8a between a plug 4 and a first connector 10a. This embodiment further comprises a second extension 8b between the plug 4 and a second connector 10b. FIG. 5 shows the plug 4 with portions of first and second pathways 16, 18 that extend through the plug 4 and from the plug 4 through first and second extensions 8a, 8b, respectively, to the standardized connectors 10a, 10b, respectively. At least one of, preferably both of first and second extensions 8a, 8b may be made of flexible tubes. The plug 4 of FIG. 5 may comprise any of or any combination of the features described for plugs herein. The embodiment of FIG. 5 is adapted to have at least a portion of plug 4, and optionally portions of first and second extension 8a, 8b, inserted into the lumen of a graft, when installed on the graft. The graft may be any of the other grafts described herein, e.g., the graft 28 of any of the other Figures. Preferably, the connectors 10a, 10b as well as at least a portion, preferably at least a 100 mm long proximal portion of each of the extensions 8a, 8b remains outside the graft, when installed in accordance with the present invention. Thereby, the aortic graft occluder 2 according to FIG. 5 may provide additional flexibility, which may facilitate the connection of a feed line (not shown) and optionally of a discharge line (not shown), e.g. to connectors 10a, 10b, respectively.

Figure 6A:
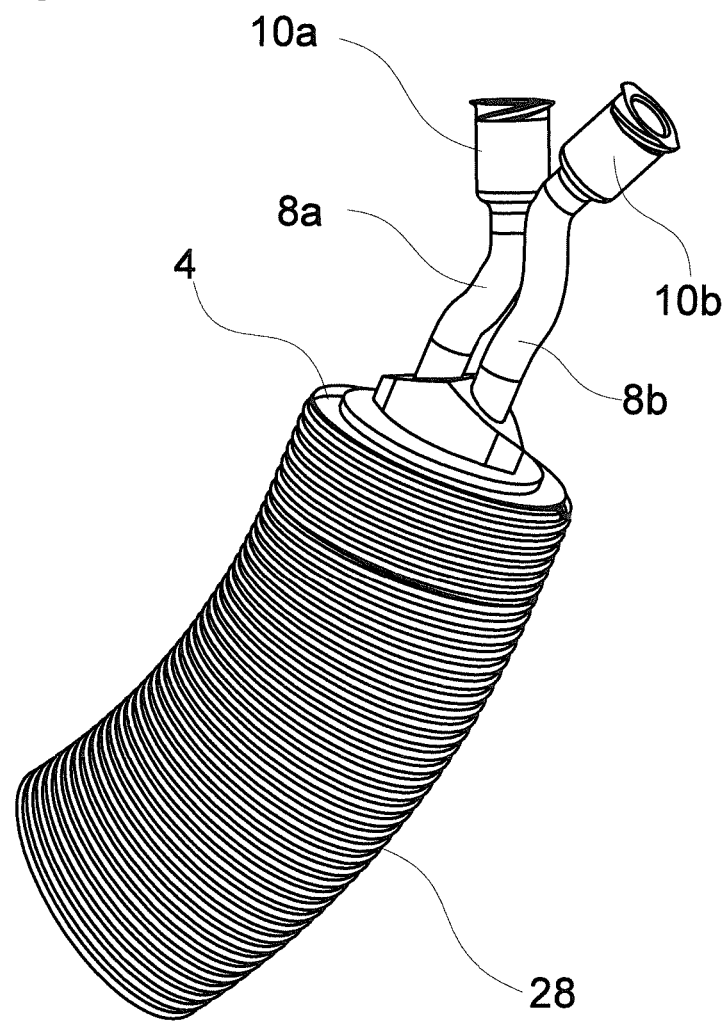
FIG. 6A shows another embodiment of an aortic graft occluder according to the invention in a perspective view.
Figure 6B:
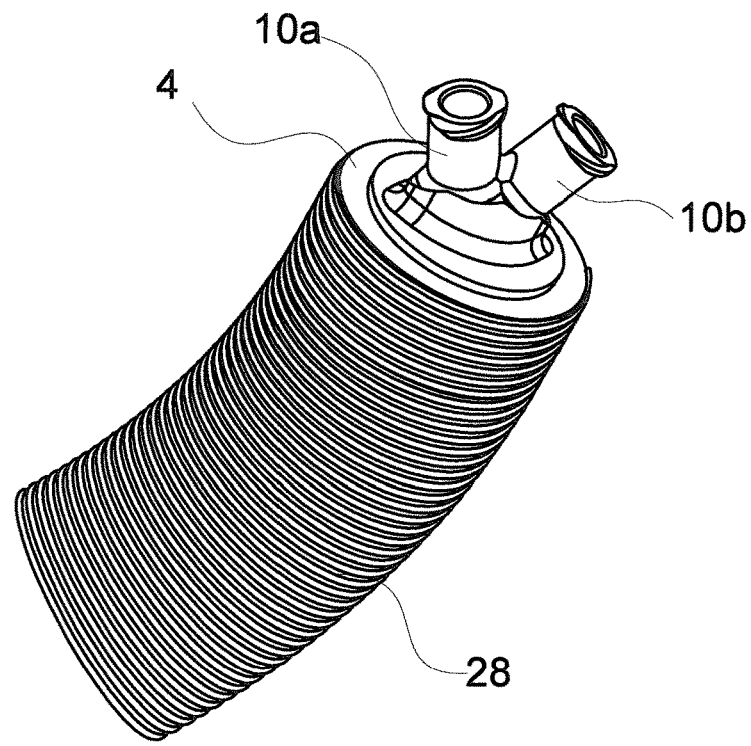
FIG. 6B shows another embodiment of an aortic graft occluder according to the invention in a perspective view.

FIGS. 6A and 6B show a schematic drawing of another embodiment of the present invention. FIG. 6A shows an embodiment of an aortic graft occluder 2 that is integrally formed with a graft 28, e.g. any of the grafts disclosed herein, e.g. graft 28 of any of the other Figures. More precisely, the plug 4 is integrally formed with the graft 28. That is to say, that the aortic graft occluder 2 may not be disconnected from the graft 28 without the destruction of at least one of the aortic graft occluder 2 and the graft 28. Preferably, the plug 4 is made from the same material as the graft 28. Alternatively, the plug 4 may comprise only some of the materials that are used in the graft 28. Optionally, the plug 4 may comprise additional materials that are not used for the construction of graft 28. As shown in FIG. 6A, the aortic graft occluder 2 may comprise a first extension 8a extending from the plug 4. The aortic graft occluder 2 may comprise a first connector 10a. The aortic graft occluder 2 may, as shown in FIG. 6A, have the first extension 8a extending from the plug 4 to a first connector 10a. The aortic graft occluder 2 may further comprise a second extension 8b and/or a second connector 10b. The second extension 8b may extend between the plug 4 and the second connector 10b. First and second connectors 10a, 10b may be standardized connectors, preferably Luer type connectors, more preferably Luer locks. The first and second extensions 8a, 8b may be made from flexible tubes, respectively. As previously explained, this may add flexibility to the aortic graft occluder 2, which may help in facilitating the procedure of connecting a feed line (not shown) and/or a discharge line (not shown) to the aortic graft occluder 2 via the first connector 10a and/or the second connector 10b, respectively. With the embodiment of FIG. 6, the usage of the aortic graft occluder 2 differs slightly from the usage of other embodiments. While other embodiments may be removed from the graft after usage, and thus be reused, e.g., in other surgeries, the embodiment of FIG. 6 is preferably designed as a single-use embodiment. As the graft 28 and the aortic graft occluder 2 of FIG. 6A are integrally formed, the graft 28 with the aortic graft occluder 2 is configured for being connected to a patient's vessel at the distal end of the graft 28. Then, a leak tightness test and/or an aortic valve functionality test as described above may be carried out. After these tests, the aortic graft occluder 2 has to be removed from the graft 28 in order to continue with the next steps of the surgery, that is to say, in order to be able to connect the other, still free, unconnected end of the graft 28 to the patient's body. In order to do so, the aortic graft occluder 2 has to be cut, clipped and/or ripped off or otherwise separated from the graft 28, for example, by using scissors, a wire cutter and/or any other suitable tool. This implies that a person selecting an aortic graft occluder 2 that is integrally formed with the graft 28 for a surgery has to take into account the future shortening that will be caused by the removal of the aortic graft occluder 2 from the graft 28 when selecting an appropriate graft of an appropriate length for a patient.

FIG. 6B shows another embodiment in accordance with the present invention. The schematic drawing of FIG. 6B shows an embodiment that resembles the embodiment of FIG. 6A in that an aortic graft occluder 2 is integrally formed with a graft 28. More precisely, a plug 4 is integrally formed with the graft 28. However, in this embodiment, first and second connectors 10a, 10b that lead to first and second pathways are directly sitting on plug 4 without one or more extensions between the plug 4 and the first and second connectors 10a, 10b, respectively. Such an embodiment may be easier for manufacturing. As the graft has to be cut during surgery anyway (similarly to the embodiment of FIG. 6B), the flexible graft 28 may be selected to have a length providing a required flexibility for an easy connection of, e.g., a feed line and/or a discharge line (the latter both not shown in FIG. 6B).

Figure 7A:
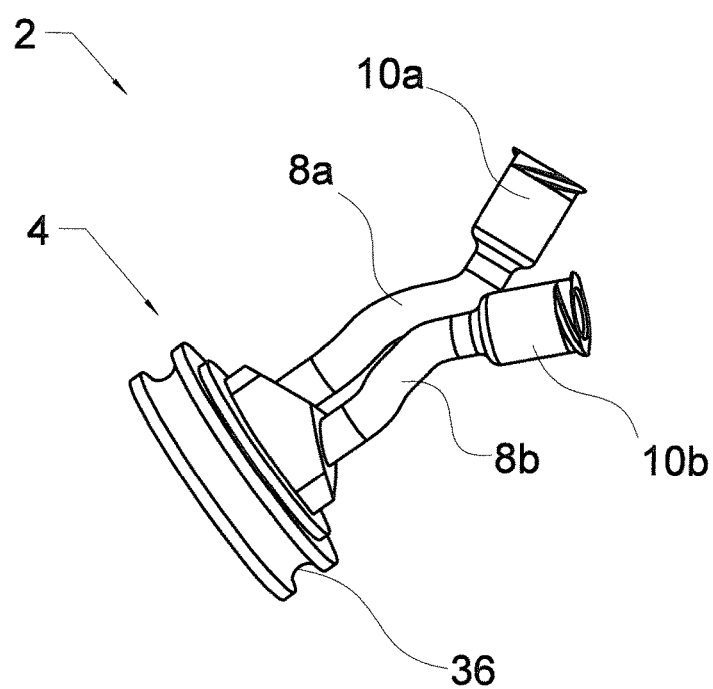
FIG. 7A shows another embodiment of an aortic graft occluder according to the invention in a perspective view.

FIG. 7A shows a schematic illustration of another embodiment of an aortic graft occluder 2 according to the present invention. FIG. 7A shows the aortic graft occluder 2 with a plug 4 having the shape of a short cylinder. The cylindrically shaped plug 4 comprises a circumferential notch 36 on the side wall of the short cylinder forming the plug 4. In the embodiment of FIG. 7A, the notch 36 has a semi-circular cross-sectional shape. However, any other suitable shape such as V-shaped, U-shaped and/or partially polygonal is contemplated. The aortic graft occluder 2 may comprise first and second extensions 8a, 8b, as shown in FIG. 7A. First extension 8a and/or second extension 8b may be made from flexible tubes. First and second extensions 8a, 8b may extend to first and second connectors 10a, 10b, respectively. Alternatively, first and second connectors 10a, 10b may directly sit on the plug 4 without first and second extension 8a, 8b.

Figure 7B:
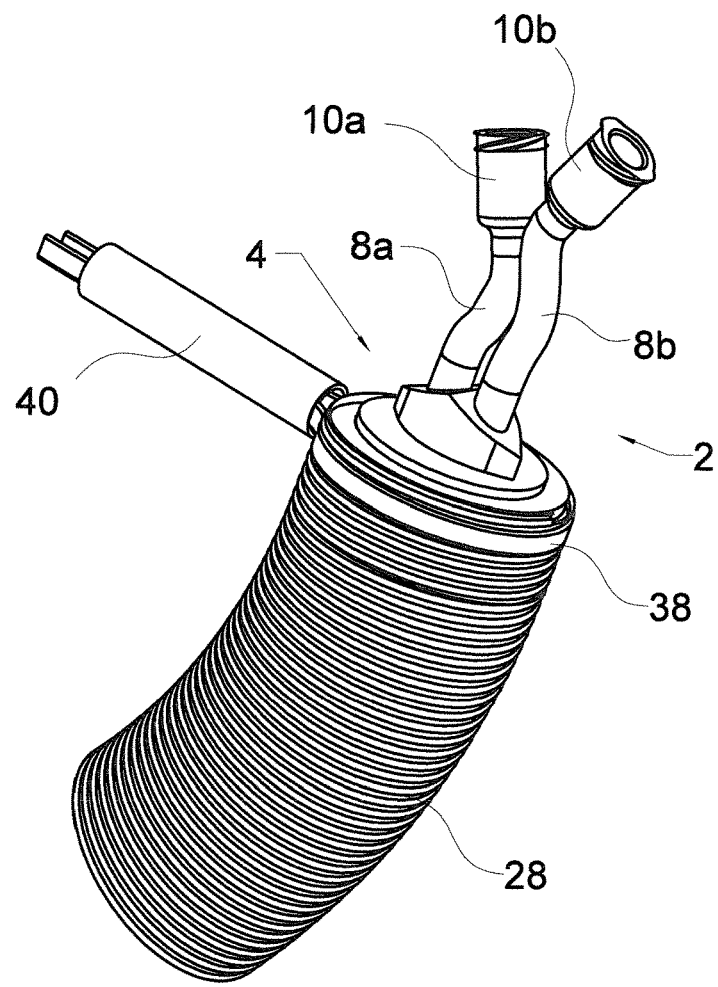
FIG. 7B shows the embodiment of FIG. 7A attached to a graft in a perspective view.

Independently from the location of the first and second connectors 10a, 10b, the usage of the embodiment shown in FIG. 7A includes positioning the plug 4 of the aortic graft occluder 2 within the lumen of a graft with the notch 36 running substantially along the interior surface of the graft. In order to attach the aortic graft occluder 2 to a graft, a sling may be used. FIG. 7B shows the aortic graft occluder 2 of FIG. 7A attached to a graft 28 by means of a sling 38 as a locking means. Sling 38 may be made from a wire, a string, a filament, a ligature and/or any other filamentous means, or any combination thereof.

Figure 7C:
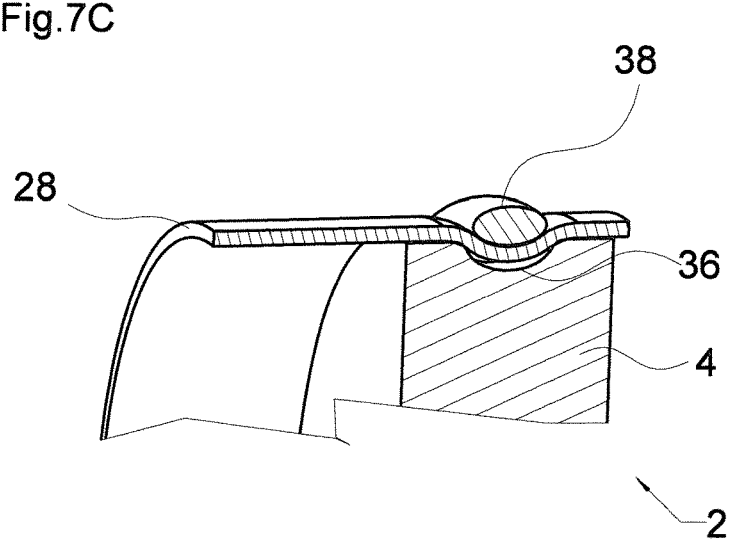
FIG. 7C shows a cross section of a detail of the embodiment of FIG. 7A attached to a graft as shown in FIG. 7B.

In FIG. 7B, the plug 4 of the aortic graft occluder 2 has been inserted into the graft 28 and the sling 38 has been wound around the outer surface of the graft 28. The sling 38 has been positioned along the circumferential notch 36 of plug 4. Consequently, notch 36 and sling 38 run along the wall of the graft 28 in parallel but on opposite sides of the wall. In order to correctly install the aortic graft occluder 2 to the graft 28, that is to say, to attach the aortic graft occluder 2 to the graft 28, the sling 38 has been tightened such that the sling 38 presses the graft 28 into the notch 36 (see the cross section in FIG. 7C). Although depicted with a slight gap between the graft 28 and the surface of the notch 36, it is contemplated that the sling 38 may press the graft against the surface of the notch such that the graft is in contact with the surface of the notch. In FIG. 7B, an optional fixation means 40 is used for keeping the sling in the tightened position but other mechanisms, e.g. forming a knot, are contemplated.

It is within the scope of the invention that any embodiment may comprise any of the afore-mentioned features alone or in any combination thereof, unless explicitly otherwise stated.

The invention claimed is:

1. An aortic graft occluder for intraoperative leak testing of a tubular aortic graft attached to an aortic root, the aortic graft occluder comprising:
 a plug adapted for sealingly closing an opening of the aortic graft,
 wherein the plug comprises a first pathway adapted for connecting a lumen of the aortic graft with a feed line, and
 wherein the aortic graft occluder comprises a second pathway, the second pathway serving as an outlet wherein the aortic graft occlude is configured to provide a fluid-tight connection between the graft and the feed line for an intramural pressure of at least 70 mmHg.

2. The aortic graft occluder of claim 1, wherein the first pathway extends to a standardized connector adapted for sealingly connecting with the feed line.

3. The aortic graft occluder of claim 1, wherein the second pathway extends to a standardized connector.

4. An aortic graft occluder for intraoperative leak testing of a tubular aortic graft attached to an aortic root, the aortic graft occluder comprising:
 a plug adapted for sealingly closing an opening of the aortic graft,
 wherein the plug comprises a first pathway adapted for connecting a lumen of the aortic graft with a feed line,
 wherein the plug is adapted to be at least partially inserted into the lumen of the graft and connected thereto,
 wherein the plug comprises a sealing section for creating a seal between the plug and the graft, and
 wherein the plug comprises an external thread adapted to be screwed into the opening of the graft wherein the aortic graft occlude is configured to provide a fluid-tight connection between the graft and the feed line for an intramural pressure of at least 70 mmHg.

5. An aortic graft occluder for intraoperative leak testing of a tubular aortic graft attached to an aortic root, the aortic graft occluder comprising:
 a plug adapted for sealingly closing an opening of the aortic graft,
 wherein the plug comprises a first pathway adapted for connecting a lumen of the aortic graft with a feed line; and
 wherein the aortic graft occluder comprises an extension extending from the plug,
 wherein the first pathway extends through the extension, the extension being configured to remain at least partially outside the lumen of the aortic graft wherein the aortic graft occlude is configured to provide a fluid-tight connection between the graft and the feed line for an intramural pressure of at least 70 mmHg.

6. The aortic graft occluder of claim 5 further comprising a locking means that is adapted to press a portion of the graft against the plug.

7. The aortic graft occluder of claim 6, wherein the extension comprises an external thread and the locking means comprises an internal thread matching the external thread of the extension, the locking means being configured to be driven along the external thread whereby at least a portion of the graft is pressed against the plug and the sealing section.

8. The aortic graft occluder of claim 7, wherein the locking means comprises an internal, tapered section for pressing at least a portion of the graft against the plug and the sealing section.

9. The aortic graft occluder of claim 7, wherein the locking means is secured to the aortic graft occluder so as to form a functional unit for use, wherein the locking means is removable from the plug and the extension.

10. The aortic graft occluder of claim 6, wherein the plug comprises a notch adapted to receive the portion of the aortic graft, wherein the locking means is adapted to press the portion of the aortic graft into the notch.

11. The aortic graft occluder of claim 1, wherein the aortic graft occluder comprises one or a combination of biocompatible materials.

12. An aortic graft occluder for intraoperative leak testing of a tubular aortic graft attached to an aortic root, the aortic graft occluder comprising:
   a plug adapted for sealingly closing an opening of the aortic graft,
   wherein the plug comprises a first pathway adapted for connecting a lumen of the aortic graft with a feed line wherein the aortic graft occlude comprises a second pathway, the second pathway serving as an outlet,
   wherein the plug comprises a third pathway adapted for serving as a sealable inlet for a medical device.

13. The aortic graft occluder of claim 1, wherein intraoperative leak testing of the tubular aortic graft comprises (i) testing tightness of a connection of the tubular aortic graft to the aortic root, or (ii) testing tightness of an aortic valve, or (iii) testing tightness of a connection of the tubular aortic graft to the aortic root and testing tightness of an aortic valve.

14. A method for leak testing of a tubular aortic graft having a distal end attached to an aortic root and having a free, proximal end by means of the aortic graft occluder according to claim 1, the method comprising the steps of:

a) sealingly attaching the aortic graft occluder to the free end of the graft;
b) fluidly connecting the lumen of the aortic graft with a feed line by connecting a first pathway of the aortic graft occluder to the feed line, wherein the feed line is configured to provide fluid to the first pathway;
c) inserting an amount of fluid into the lumen, thereby creating an intraluminal pressure above atmospheric pressure and maintaining the intraluminal pressure;
d) checking the attachment of the distal end of the aortic graft to the aortic root for leakproofness by checking for fluid leaking from the attachment, or checking functionality of an aortic valve by verifying tightness of the closed aortic valve, or checking the attachment of the distal end of the aortic graft to the aortic root for leakproofness by checking for fluid leaking from the attachment and checking functionality of an aortic valve by verifying tightness of the closed aortic valve; and
e) removing the aortic graft occluder from the graft.

15. The method according to claim 14, wherein the plug comprises a third pathway adapted for serving as a sealable inlet for a medical device, and wherein step c) further comprises the step of sealingly closing at least one of the second pathway and the third pathway.

16. The method according to claim 15, wherein step c) further comprises removing substantially all gas from the lumen of the aortic graft via the second pathway and/or the third pathway before sealingly closing the second pathway and/or the third pathway.

* * * * *